United States Patent
Calderon et al.

(10) Patent No.: US 7,397,044 B2
(45) Date of Patent: Jul. 8, 2008

(54) IMAGING MODE FOR LINEAR ACCELERATORS

(75) Inventors: Edward Lewis Calderon, Pittsburg, CA (US); Francisco M. Hernadez-Guerra, Concord, CA (US); Ali Bani-Hashemi, Walnut Creek, CA (US); Farhad A. Ghelmansarai, Danville, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 331 days.

(21) Appl. No.: 11/187,660

(22) Filed: Jul. 21, 2005

(65) Prior Publication Data

US 2007/0018117 A1     Jan. 25, 2007

(51) Int. Cl.
*G01N 23/04* (2006.01)
*A61N 5/00* (2006.01)
*G21G 5/00* (2006.01)

(52) U.S. Cl. ............ 250/492.1; 250/492.3; 250/370.08; 250/370.09; 378/62

(58) Field of Classification Search .............. 250/492.1; 378/62
See application file for complete search history.

(56) References Cited

U.S. PATENT DOCUMENTS

| | | | | |
|---|---|---|---|---|
| 4,763,343 A * | 8/1988 | Yanaki | ........................ | 378/110 |
| 4,868,843 A * | 9/1989 | Nunan | ........................ | 378/152 |
| 5,182,056 A * | 1/1993 | Spence et al. | ................ | 264/401 |
| 5,369,678 A * | 11/1994 | Lee et al. | ..................... | 718/104 |
| 5,471,516 A * | 11/1995 | Nunan | ........................ | 378/65 |
| 5,621,779 A | 4/1997 | Hughes et al. | | |
| 6,038,284 A * | 3/2000 | Hernandez-Guerra et al. | . | 378/65 |
| 6,052,435 A * | 4/2000 | Hernandez-Guerra et al. | .... | 378/150 |
| 6,108,399 A * | 8/2000 | Hernandez-Guerra et al. | . | 378/65 |
| 6,118,847 A * | 9/2000 | Hernandez-Guerra et al. | . | 378/65 |
| 6,198,957 B1 * | 3/2001 | Green | ........................ | 600/411 |
| 6,240,162 B1 * | 5/2001 | Hernandez-Guerra et al. | . | 378/65 |
| 6,445,766 B1 * | 9/2002 | Whitham | ..................... | 378/65 |
| 6,459,762 B1 | 10/2002 | Wong et al. | | |
| 6,493,424 B2 * | 12/2002 | Whitham | ..................... | 378/137 |
| 6,618,466 B1 * | 9/2003 | Ning | ........................... | 378/62 |
| 6,828,571 B1 * | 12/2004 | McCord et al. | .......... | 250/492.2 |
| 7,180,981 B2 * | 2/2007 | Wang | ......................... | 378/124 |

(Continued)

OTHER PUBLICATIONS

"Primus & Primus Plus Linear Accelerator User Manual", Revision G Dec. 2004, Siemens Medical Solutions USA, Inc. 374pgs.

*Primary Examiner*—David A. Vanore
*Assistant Examiner*—Bernard Souw

(57) ABSTRACT

Some embodiments include reception of a first instruction to enter an imaging mode, and, in response to the first instruction, automatic performance of at least one of: reduction of a focal spot size of a radiation beam, movement of a flattening filter out of a path of the radiation beam, replacement of a first target for photon emission with a second target for photon emission, or movement of a scatter-reducing filter into the path of the radiation beam. Embodiments may further include reception of a second instruction to enter a first radiation treatment mode, and, in response to the second instruction, automatic performance at least one of: increase of a focal spot size of the radiation beam, movement of the flattening filter into the path of the radiation beam, replacement of the second target with the first target, or movement of the scatter-reducing filter out of the path of the radiation beam.

19 Claims, 9 Drawing Sheets

U.S. PATENT DOCUMENTS

| | | |
|---|---|---|
| 7,242,742 B2 * | 7/2007 | Calderon et al. ............... 378/65 |
| 2002/0115932 A1 * | 8/2002 | Kennedy et al. ............ 600/424 |
| 2003/0164172 A1 * | 9/2003 | Chumas et al. ............. 128/898 |
| 2005/0169434 A1 * | 8/2005 | McNeirney et al. ......... 378/206 |
| 2005/0226377 A1 * | 10/2005 | Wong et al. .................... 378/65 |
| 2006/0163495 A1 * | 7/2006 | Hiramoto et al. ......... 250/492.3 |
| 2006/0256925 A1 * | 11/2006 | Virshup et al. .............. 378/158 |
| 2007/0018117 A1 * | 1/2007 | Calderon et al. ......... 250/492.1 |

* cited by examiner

IMAGING MODE FOR LINEAR ACCELERATORS

BACKGROUND

1. Field

The embodiments described herein relate generally to linear accelerators. More particularly, the described embodiments relate to linear accelerators providing multiple operating modes.

2. Description

A linear accelerator produces electrons or photons having particular energies. In one common application, a linear accelerator produces a radiation beam used for medical radiation treatment. The beam may be directed toward a target area of a patient in order to destroy cells within the target area by causing ionizations within the cells or other radiation-induced cell damage.

Radiation treatment plans are designed to maximize radiation delivered to a target while minimizing radiation delivered to healthy tissue. However, designers of a treatment plan assume that relevant portions of a patient will be in a particular position relative to a linear accelerator during delivery of the treatment radiation. If the relevant portions are not positioned exactly as required by the treatment plan, the goals of maximizing target radiation and minimizing healthy tissue radiation may not be achieved. More specifically, errors in positioning the patient can cause the delivery of low radiation doses to tumors and high radiation doses to sensitive healthy tissue. The potential for misdelivery increases with increased positioning errors.

Conventional imaging systems may be used to determine a patient position prior to treatment according to a particular radiation treatment plan. For example, a radiation beam is emitted by a linear accelerator, passes through a volume of the patient and is received by an imaging system. The imaging system generates a two-dimensional portal image of the patient volume, which can be used to determine whether the patient is in a position dictated by the particular treatment plan.

The foregoing imaging systems may be both ineffective and inefficient. For example, the radiation beam generated by a linear accelerator for imaging may deliver a dose rate that is significantly less than a dose rate used for radiation treatment, but other characteristics of the beam may be unsuitable for imaging. Moreover, no efficient systems exist for changing these characteristics such that the resulting beam is suitable for imaging.

SUMMARY

In order to address the foregoing, some embodiments provide a system, method, apparatus, and means to receive a first instruction to enter an imaging mode, and, in response to the first instruction, automatically perform at least one of: reducing a focal spot size of a radiation beam, moving a flattening filter out of a path of the radiation beam, replacing a first target for photon emission with a second target for photon emission, or moving a scatter-reducing filter into the path of the radiation beam. Embodiments may further include reception of a second instruction to enter a first radiation treatment mode, and, in response to the second instruction, automatic performance at least one of: increase of a focal spot size of the radiation beam, movement of the flattening filter into the path of the radiation beam, replacement of the second target with the first target, or movement of the scatter-reducing filter out of the path of the radiation beam.

According to some aspects, the second instruction comprises an instruction to enter a photon radiation treatment mode, a third instruction is received to enter an electron radiation treatment mode, and, in response to the third instruction, the first target or the second target is automatically moved out of the path of the radiation beam so that neither the first target or the second target is in the path of the radiation beam.

Some embodiments include an input device to receive a first instruction to enter an imaging mode, and a second instruction to enter a first radiation treatment mode, and an accelerator waveguide to emit a radiation beam. Also included in these embodiments is at least one of a first device to reduce a focal spot size of a radiation beam in response to the first instruction, and to increase a focal spot size of the radiation beam in response to the second instruction, a second device to move a flattening filter out of a path of the radiation beam in response to the first instruction, and to move the flattening filter into the path of the radiation beam in response to the second instruction, a third device to replace a first target for photon emission with a second target for photon emission in response to the first instruction, and to replace the second target with the first target in response to the second instruction, or a fourth device to move a scatter-reducing filter into the path of the radiation beam in response to the first instruction, and to move the scatter-reducing filter out of the path of the radiation beam in response to the second instruction.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
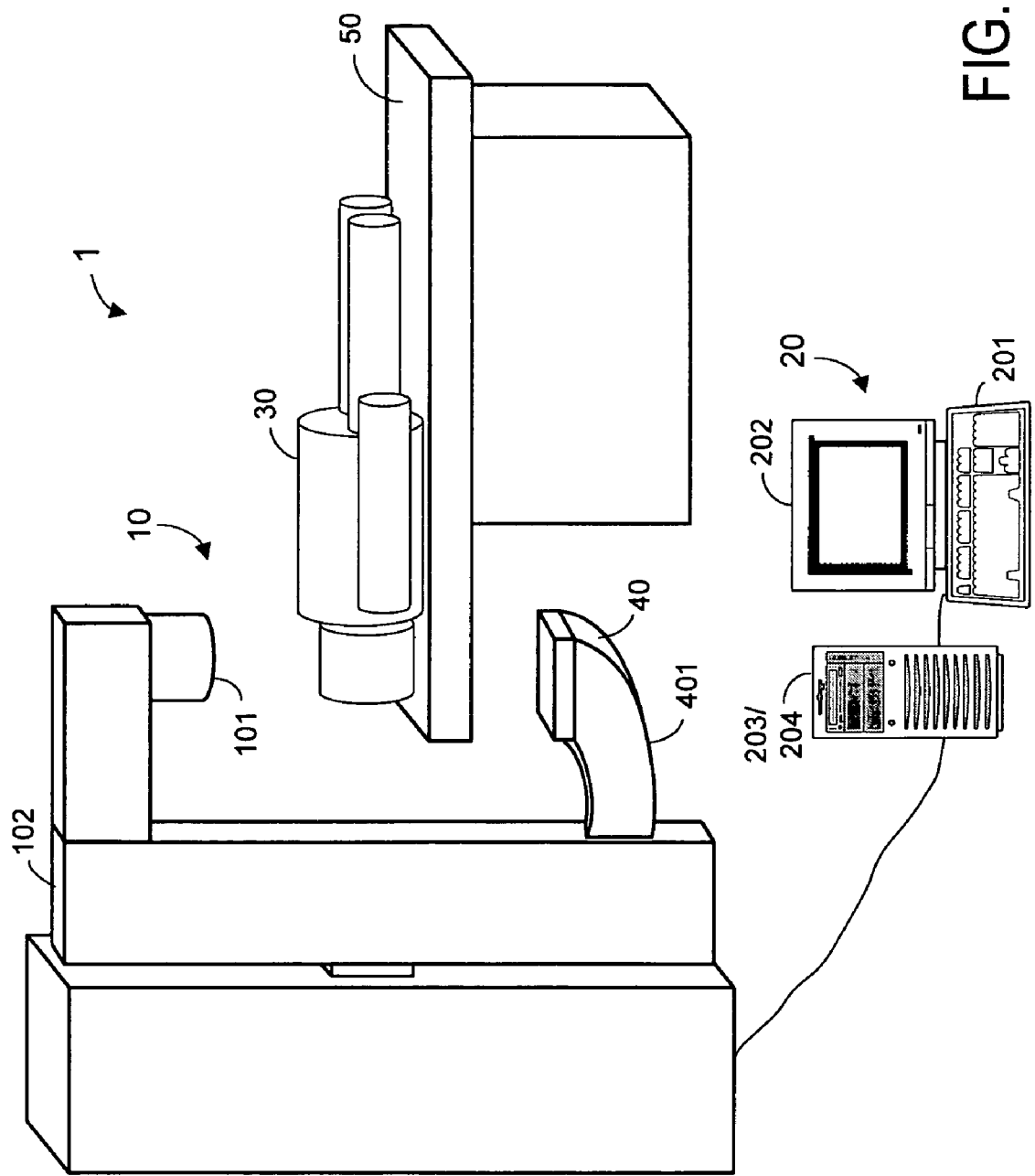
FIG. 1 is a perspective view of a linear accelerator system according to some embodiments.

FIG. 1 is a perspective view of system 1 according to some embodiments. Shown are linear accelerator 10, operator console 20, beam object 30, imaging device 40 and table 50.

System 1 may be used to generate radiation for imaging and/or for medical radiation treatment. In this regard, beam object 30 comprises a patient positioned to receive treatment radiation according to a radiation treatment plan. System 1 may be employed in other applications according to some embodiments.

In one example according to some embodiments, a first instruction to enter an imaging mode is received, and, in response to the first instruction, at least one of the following is automatically performed: reducing a focal spot size of a radiation beam, moving a flattening filter out of a path of the radiation beam, replacing a first target for photon emission with a second target for photon emission, or moving a scatter-reducing filter into the path of the radiation beam. Embodiments may further include reception of a second instruction to enter a first radiation treatment mode, and, in response to the second instruction, automatic performance at least one of: increase of a focal spot size of the radiation beam, movement of the flattening filter into the path of the radiation beam, replacement of the second target with the first target, or movement of the scatter-reducing filter out of the path of the radiation beam.

Linear accelerator 10 may deliver a radiation beam from treatment head 101 toward a volume of object 30 that is located at an isocenter of accelerator 10. According to some embodiments, the radiation beam may comprise photon or electron radiation having various energies. Various implementations of treatment head 101 according to some embodiments are described below.

Imaging device 40 may comprise any system to acquire an image based on received photon radiation (i.e., X-rays) and/or electron radiation. Imaging device 40 acquires images that are used before, during and after radiation treatment. For example, imaging device 40 may be used to acquire images for diagnosis, verification and recordation of a patient position, and verification and recordation of an internal patient portal to which treatment radiation is delivered. As described above, the effectiveness of radiation treatment often depends on the quality of the acquired images.

In some embodiments, imaging device 40 is a flat-panel imaging device using a scintillator layer and solid-state amorphous silicon photodiodes deployed in a two-dimensional array. The RID1640, offered by Perkin-Elmer®, Inc. of Fremont, Calif., is one suitable device. In other embodiments, imaging device 40 converts X-rays to electrical charge without requiring a scintillator layer. In such imaging devices, X-rays are absorbed directly by an array of amorphous selenium photoconductors. The photoconductors convert the X-rays directly to stored electrical charge that comprises an acquired image of a radiation field. Imaging device 40 may also comprise a CCD or tube-based camera. Such an imaging device may include a light-proof housing within which are disposed a scintillator, a mirror, and a camera.

Imaging device 40 may be attached to gantry 102 in any manner, including via extendible and retractable housing 401. Gantry 102 is rotatable around an axis before, during and after emission of the radiation beam. Rotation of gantry 102 may cause treatment head 101 and imaging device 40 to rotate around the isocenter such that the isocenter remains located between treatment head 101 and imaging device 40 during the rotation.

Table 50 supports object 30 during radiation therapy. Table 50 is adjustable to ensure, along with rotation of gantry 102, that a volume of interest is positioned between treatment head 101 and imaging device 40. Table 50 may also be used to support devices used for acquisition of correction images, other calibration tasks and/or beam verification.

Operator console 20 includes input device 201 for receiving instructions from an operator and output device 202, which may be a monitor for presenting operational parameters of linear accelerator 10 and/or interfaces for receiving instructions. Such instructions may include an instruction to enter an imaging mode and an instruction to enter a treatment mode. Output device 202 may also present images acquired by imaging device 40 to verify patient positioning prior to radiation treatment. Input device 201 and output device 204 are coupled to processor 203 and storage 204.

Processor 203 executes program code according to some embodiments. The program code may be executable to control system 1 to operate as described herein. The program code may be stored in storage 204, which may comprise one or more storage media of identical or different types, including but not limited to a fixed disk, a floppy disk, a CD-ROM, a DVD-ROM, a Zip™ disk, a magnetic tape, and a signal. Storage 204 may, for example, store a software application to provide radiation treatment, radiation treatment plans, portal images, and other data used to perform radiation treatment. The other data may include sets of hard-coded parameters for various elements of system 1, or "soft pots", that are associated with various functions of system 1. For example, one set of soft pots may be associated with an imaging mode, another set of soft pots may be associated with an X-ray treatment mode, and while another set of soft pots may be associated with an electron treatment mode.

Operator console 20 may be located apart from linear accelerator 10, such as in a different room, in order to protect its operator from radiation. For example, accelerator 10 may be located in a heavily shielded room, such as a concrete vault, which shields the operator from radiation generated by accelerator 10.

Each of the devices shown in FIG. 1 may include less or more elements than those shown. In addition, embodiments are not limited to the devices shown in FIG. 1.

Figure 2:
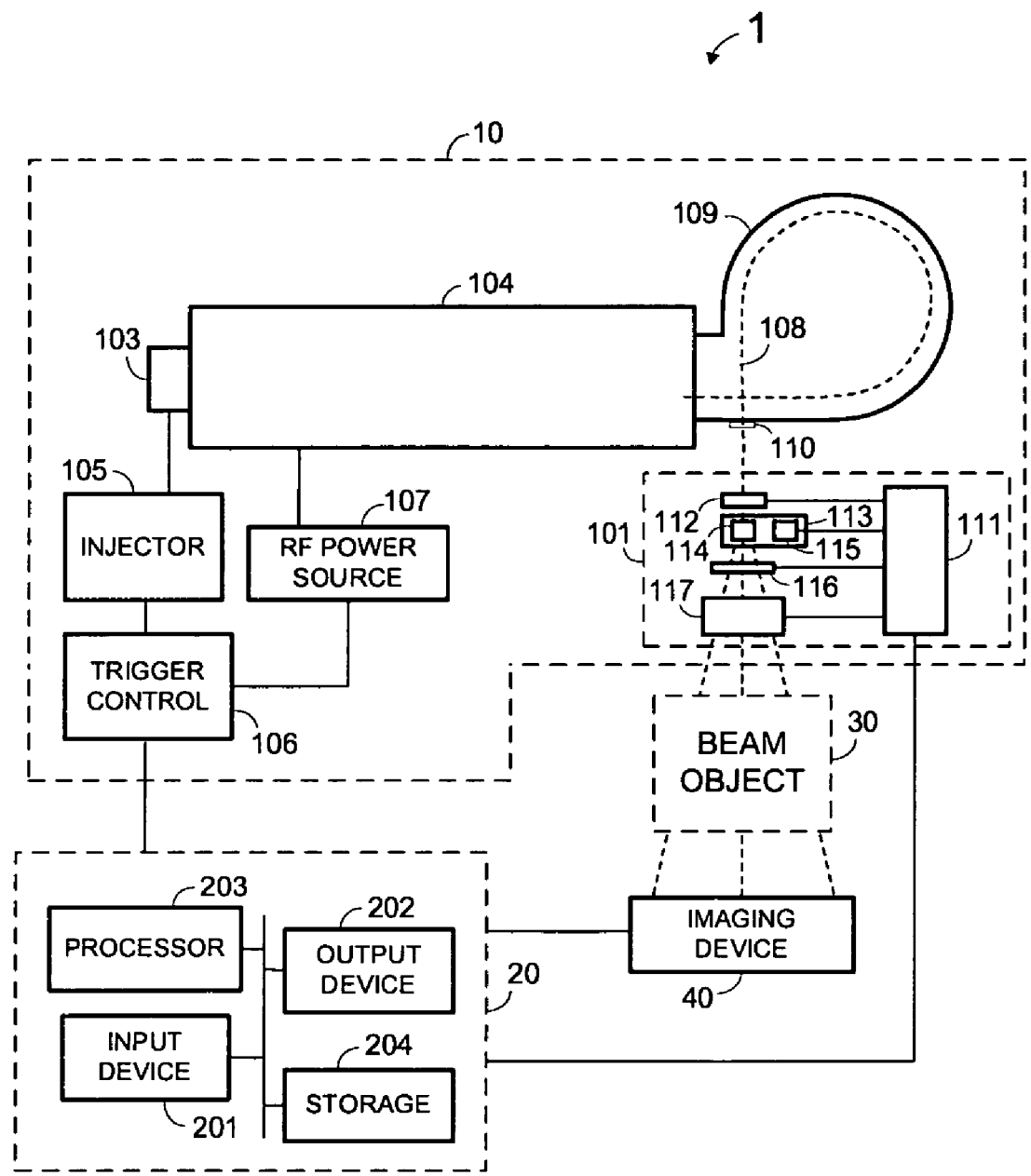
FIG. 2 is a block diagram of a linear accelerator system according to some embodiments.

FIG. 2 is a block diagram of system 1 showing internal elements of linear accelerator 10, operator console 20, and imaging device 40 according to some embodiments. Embodiments may differ from that shown in FIG. 2 and/or from that shown in FIG. 1.

Linear accelerator 10 of FIG. 2 includes electron source 103 for injecting electrons into accelerator waveguide 104. Source 103 may comprise an electron gun including a heater, a cathode (thermionic or other type), a control grid (or diode gun), a focus electrode, an anode, and other elements. An injector current sourced by particle source 103 may be controlled by injector pulses received from injector 105. Injector 105 may, in turn, receive trigger signals from trigger control 106 and control the amplitude of the injector pulses by a control grid bias voltage applied to source 103.

Accelerator waveguide 104 includes cavities that are designed and fabricated so that electric currents flowing on their surfaces generate electric fields that are suitable to accelerate the electrons. The oscillation of these electric fields within each cavity is delayed with respect to an upstream cavity so that an electron is further accelerated as it arrives at each cavity.

The oscillating electric fields within the cavities of accelerator waveguide 104 are produced in part by an oscillating electromagnetic wave received by accelerator waveguide 104 from RF power source 107. Trigger control 106 may control RF power source 107 to generate an electromagnetic wave having a selected power and/or pulse rate. RF power source 107 may comprise any suitable currently- or hereafter-known pulsed power source. In some embodiments, RF power source 107 comprises a magnetron. RF power source 107 comprises a klystron and an RF driver in some embodiments.

Accelerator waveguide 104 may output beam 108 to bending envelope 109. Beam 108 includes a stream of electron bunches having various energies and bending envelope 109 may comprise an evacuated magnet to bend beam 108 approximately two hundred seventy degrees. Bending envelope 109 may also focus beam 108 and select one or more energies for output.

Bending envelope 109 may select an energy by establishing a magnetic field that will allow only electrons of a selected energy (or of a range of energies surrounding the selected energy) to turn two hundred seventy degrees and exit through window 110. Other bending angles and/or systems to select energies may be used.

Window 110 may comprise two metal foils with water flowing therebetween for cooling. Beam 108 enters treatment head 101 after passing through window 110. Treatment head 101 may comprise any number and arrangement of elements according to some embodiments.

Treatment head 101 of FIG. 2 includes control unit 111 which may receive control signals from operator console 20. Control unit 111 is coupled to beam focuser 112, target housing 113 including hi-Z target 114 and low-Z target 115, flattening filter 116, and other elements 117. The depiction of treatment head 101 in FIG. 2 is not intended to indicate relative sizes or spatial relationships of the elements located therein, although some embodiments may be thus reflected.

The couplings between control unit 111 and each of elements 112 through 117 may comprise mechanical and/or electrical couplings. One or more elements may reside between control unit 111 and an element to which it is shown coupled in FIG. 2. In some embodiments, control unit 111 comprises one or more separate elements, each of which is coupled to one or more of elements 112 through 117. One or more of elements 112 through 117 may be controlled directly by operator console 20 and/or by another device according to some embodiments.

The elements of treatment head 101 may be configured based on an operating mode of system 1. For example, the elements may be configured in a first arrangement if an instruction is received to enter a treatment mode, and the elements may be configured in a second arrangement if an instruction is received to enter an imaging mode. FIG. 2 illustrates an arrangement used in a treatment mode according to some embodiments.

Beam focuser 112 may comprise any suitable system to receive beam 108 and to change a focal spot size thereof. The focal spot size may refer to the profile of the beam at a location where photon emission occurs within one of targets 113 and 114. Generally, a smaller focal spot may be suitable for imaging while a larger focal spot may be suitable for delivering treatment.

In some embodiments, beam focuser 112 comprises deflector plates disposed adjacent to a path of beam 108. Control unit 111 may energize the deflector plates during emission of beam 108 in order to create a desired focal spot size. Beam focuser 112 may be used to increase the focal spot size for treatment in a case that the focal spot size would be unsuitably small in the absence of beam focuser 112. Alternatively, beam focuser 112 may be used to reduce the focal spot size for imaging in a case that the focal spot size would be unsuitably large in the absence of beam focuser 112. Treatment head 111 may include mechanical elements to move beam focuser 112 out of the path of beam 108 if a selected operating mode does not require beam focusing.

Target housing 113 includes hi-Z (i.e., high atomic weight) target 114, which may comprise Gold, Tungsten, or another suitable material. Upon receiving electron beam 108, such a target may generate photons having an energy spectrum suitable for radiation treatment. Low-Z (i.e., low atomic weight) target 115 may comprise Carbon, Aluminum, or another suitable material. Such a target may generate photons having an energy spectrum suitable for imaging in response to receipt of electron beam 108. The terms hi-Z and low-Z as used herein are not intended to indicate particular atomic weights, but only a relationship of the atomic weight of target 114 to the atomic weight of target 115.

Target housing 113 may comprise any suitable system to selectively place target 114 or target 115 in the path of beam 108. Such placement may be controlled by control unit 111. Target 114 is shown placed in the path because system 1 is in an X-ray treatment mode according to some embodiments.

Flattening filter 116 may comprise any one or more elements to improve a profile of beam 108 for treatment. In this regard, an intensity of X-ray beam 108 at beam object 30 may be highest at the center of the radiation field and may significantly decrease toward the edges of the field. Flattening filter 116 may therefore be used to provide a more even intensity distribution.

Control unit 111 may be coupled to flattening filter 116 so as to selectively place flattening filter in the path of beam 108 for a treatment mode. Flattening filter 116 may, however, increase an amount of radiation scattering, and therefore may not be suitable for an imaging mode of operation. Control unit 111 may therefore also be coupled to flattening filter 116 so as to selectively move flattening filter 116 out of the path of beam 108 for an imaging mode.

Other elements 117 may include shield blocks, dosimetry chambers, collimator plates, accessory trays and any other treatment, imaging, calibration, and verification devices as are known in the art. One or more of other elements 117 may be electrically and/or mechanically coupled to control unit 111, operator console 20, and/or to one or more other devices. For example, dosimetry chambers of other elements 117 may transmit dosimetric information directly to operator console 20. In another example, collimator plates of elements 117 may be driven to desired positions by a motor that is controlled by operator console 20.

Operator console 20 of FIG. 2 may control an injector current produced by particle source 103, and/or an amount of power generated by RF power source 107. Such control may include control of trigger control 106 to control injector 105 or RF power source 107, respectively. Operator console 20 may also control imaging device 40 to acquire an image, and may control one or more elements of treatment head 101 via control unit 111. Examples of the latter control according to some embodiments are provided below.

Figure 3:
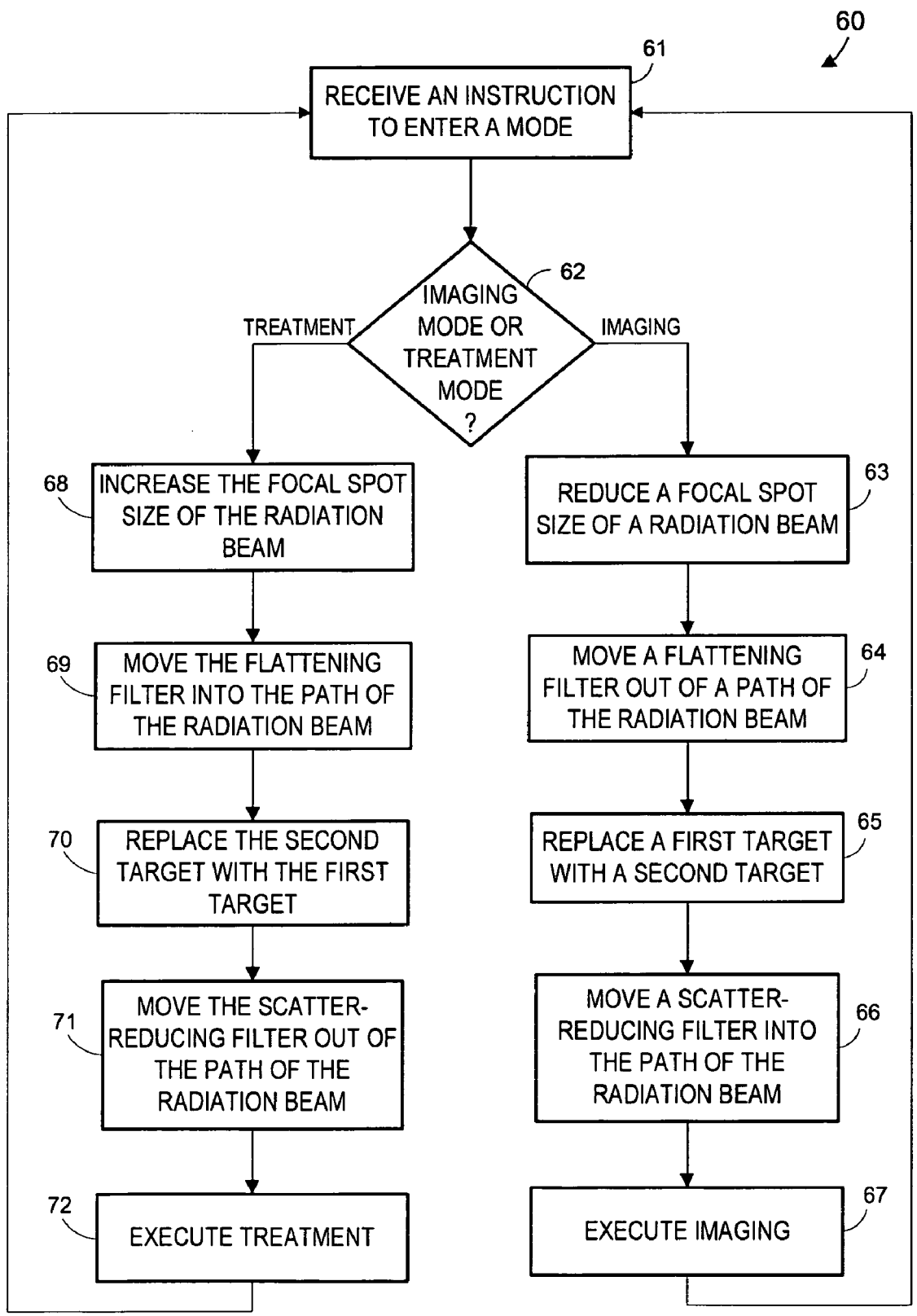
FIG. 3 is a flow diagram of process steps pursuant to some embodiments.

FIG. 3 is a flow diagram of process steps 60 according to some embodiments. Process steps 60 may be executed by one or more elements of linear accelerator 10, operator console 20, treatment head 101, control unit 111, and other devices. Accordingly, process steps 60 may be embodied in hardware and/or software. Process steps 60 will be described below with respect to the above-described elements, however it will be understood that process steps 60 may be implemented and executed differently than as described below.

Figure 4:
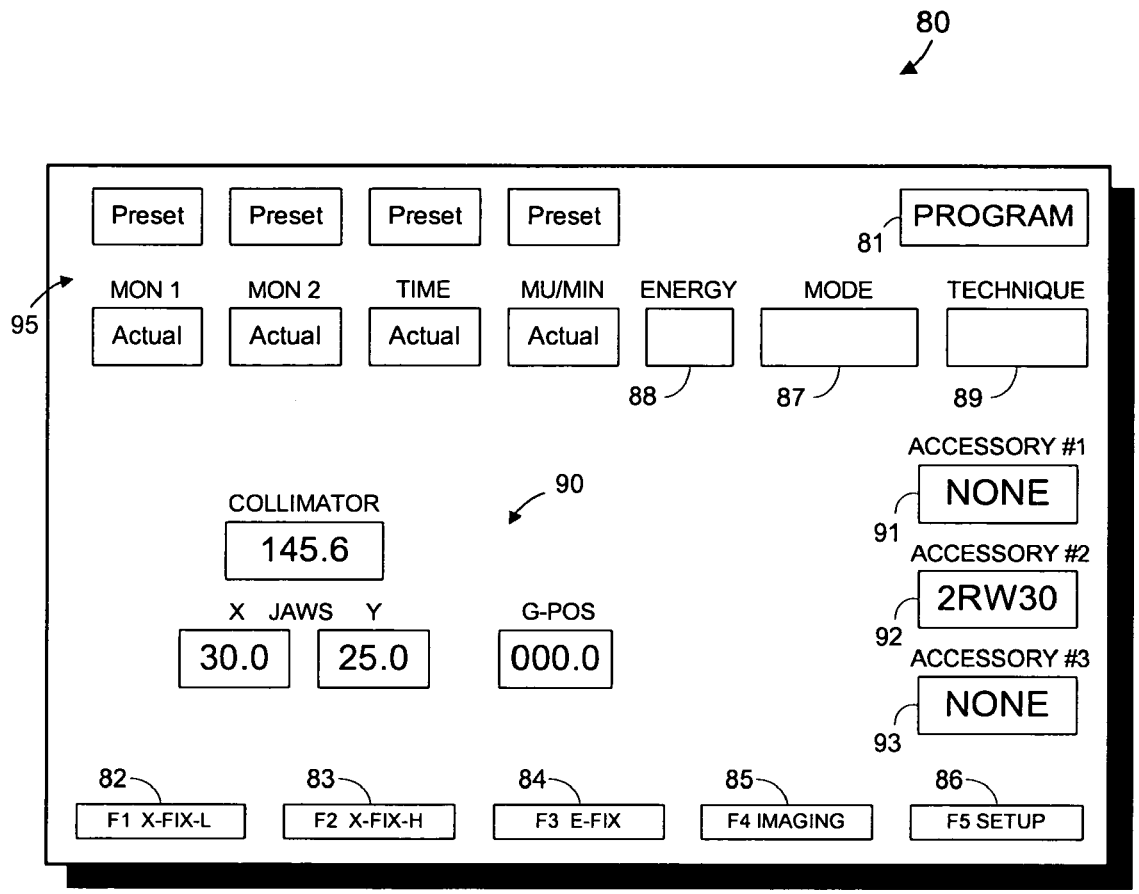
FIG. 4 is an outward view of an interface to receive instructions according to some embodiments.

Prior to step 61, an operator may use input device 201 of operator console 20 to initiate operation of system 1. In response, processor 203 may execute program code of a system control application stored in storage 204. FIG. 4 is an outward view of a user interface that is presented by output device 202 in some embodiments due to execution of the program code.

Interface 80 may be used by an operator to input instructions to system 1. Conversely, system 1 may receive the instructions via interface 80. Embodiments may utilize one or more interfaces that share zero or more features with interface 80.

In the illustrated embodiment, field 81 indicates a status of system 1. As shown, the status indicates that system 1 is being programmed. Fields 82 through 86 indicate keys of input device 201 that may be used to instruct system 1 to enter a selected operational mode. For example, function keys F1, F2, F3 and F4 (not shown) may be used to issue instructions to enter a low-energy photon radiation treatment mode, a high-energy photon radiation treatment mode, an electron radiation treatment mode, and an imaging mode, respectively.

The selected mode is displayed in field 87, with other details of the mode shown in fields 88 and 89. Fields 90 indicate a position of gantry 102 and a configuration of collimator plates of elements 117, while fields 91 through 93 identify accessories mounted in each of three accessory trays of elements 117. Fields 95 are reserved for presenting preset and actual values of dose (MON1 and MON2), beam on time (Time) and dose rate (MU/Min).

Figure 5:
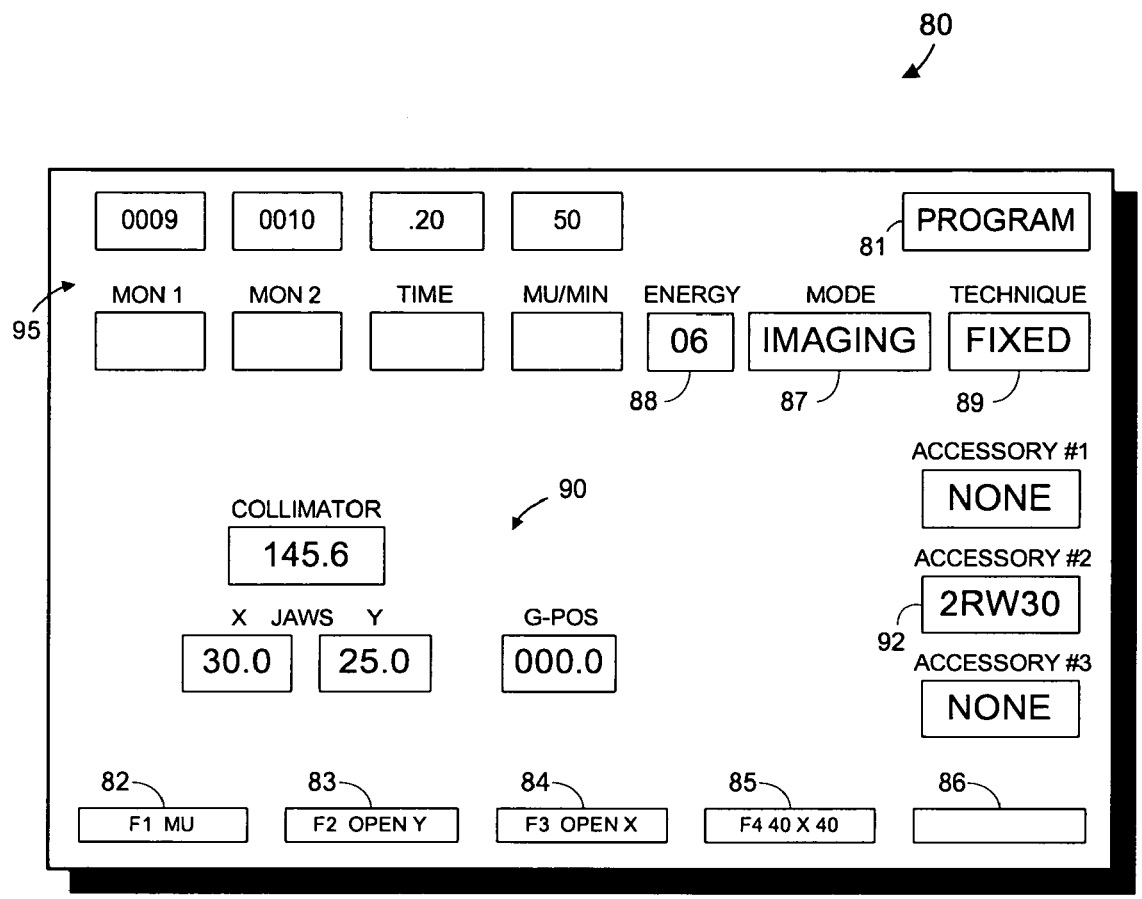
FIG. 5 is an outward view of an interface to receive instructions according to some embodiments.

At step 61, the operator selects one of function keys F1 through F4 of input device 201. It will initially be assumed that function key F4 is selected. FIG. 5 shows interface 80 after selection of function key F4 according to some embodiments. Fields 87 and 89 are automatically filled, while the operator may complete field 88 and the top row of fields 95 directly or using sub-interfaces of interface 80.

Selection of function key F4 causes the labels of fields 82 through 86 to change. According to the new labels, function keys F2, F3 and F4 may be used to control collimator plates of elements 117, and function key F1 may be used to access a sub-interface for specifying a desired dose.

After completing all required fields of interface 80 and of any sub-interfaces, an operator places system 1 into a Ready mode by pressing an Accept key of input device 201. According to the present example, detection of the pressing of the Accept key comprises receiving an instruction to enter a mode. Flow therefore proceeds to step 62 after the Accept key is pressed.

System 1 determines whether an imaging mode or a treatment mode has been selected at step 62. Continuing with the present example, a focal spot size of a radiation beam is reduced at 63 because an imaging mode has been selected. As described above, the focal spot size may be reduced by any suitable system to receive beam 108 and to change a focal spot size thereof. In some embodiments of step 63, control unit 111 energizes deflector plates of beam focuser 112 such that beam 108 will create a desired focal spot size on a target when beam 108 is generated. In this regard, step 63 may be performed prior to generation of beam 108.

Figure 6:
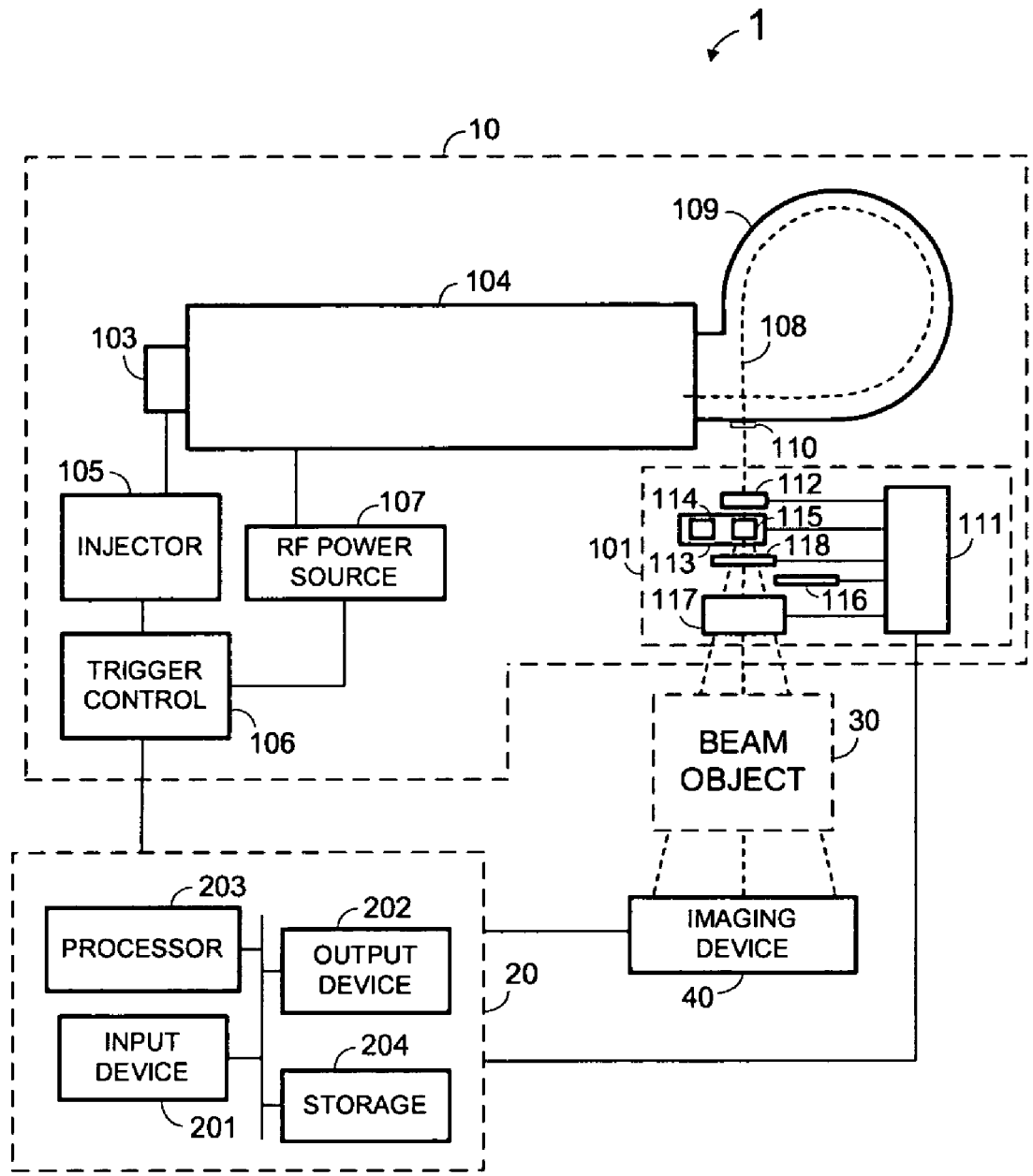
FIG. 6 is a block diagram of a linear accelerator system according to some embodiments.

A flattening filter is then moved out of a path of the radiation beam at step 64. FIG. 6 is a block diagram of system according to some embodiments. As shown, flattening filter 116 has been moved from the position shown in FIG. 2 to a position out of the path of beam 108. Any suitable mechanism may be employed to move flattening filter 116 at step 64.

Next, at step 65, a first target is replaced with a second target. FIG. 6 also shows target 115 occupying the position in the path of beam 108 that was occupied by target 114 in FIG. 2. In the illustrated embodiment, target 114 may be replaced by target 115 by moving housing 113 as shown. Any suitable systems for switching targets 114 and 115 may be employed.

A scatter-reducing filter is moved into the path of the radiation beam at 66. FIG. 6 shows scatter-reducing filter 118 in the path of radiation beam 108. Scatter radiation is believed to decrease image quality; therefore introduction of a scatter-reducing filter may increase image quality. The embodiment of FIG. 2 does not include a scatter-reducing filter.

An image is then acquired by imaging device 40 at step 67. According to some embodiments of step 67, linear accelerator 10 is controlled to emit beam 108 toward treatment head 101 at a specified energy and dose rate. Beam 108 is focused by beam focuser 112 to reduce a focal spot size thereof, and impacts target 115 to generate a divergent photon beam having an energy spectrum suitable for imaging. The photon beam passes through scatter-reducing filter 118, other elements 117, and beam object 30 before impacting imaging device 40. Imaging device 40 therefore acquires the image based on the photon beam as attenuated by beam object 30. In some embodiments, operator console 20 updates the lower row of fields 95 of interface 80 in real time during acquisition of the image.

Steps 63 through 66 may be performed under the control of control unit 111 in response to signals received from operator console 20. For example, operator console 20 may transmit a set of instructions and/or parameters associated with an imaging mode to control unit 111 after step 62. The set may be stored among one or more soft pots of storage 204.

In this regard, step 61 may comprise reception of the set of instructions and/or parameters by control unit 111 (or by another one or more elements for controlling elements of treatment head 101). More generally, steps 61 and 62 may be performed by any element of system 1, may be performed at several times by different elements of system 1, and may be performed at any time prior to step 67. Step 63 through 66 can also occur at any time before step 67.

Some embodiments include performance of only one, two, or three of steps 63 through 66. The steps of 63 through 66 that are performed may occur in any order relative to one another. Two or more of steps 63 through 66 may be performed simultaneously.

Figure 7:
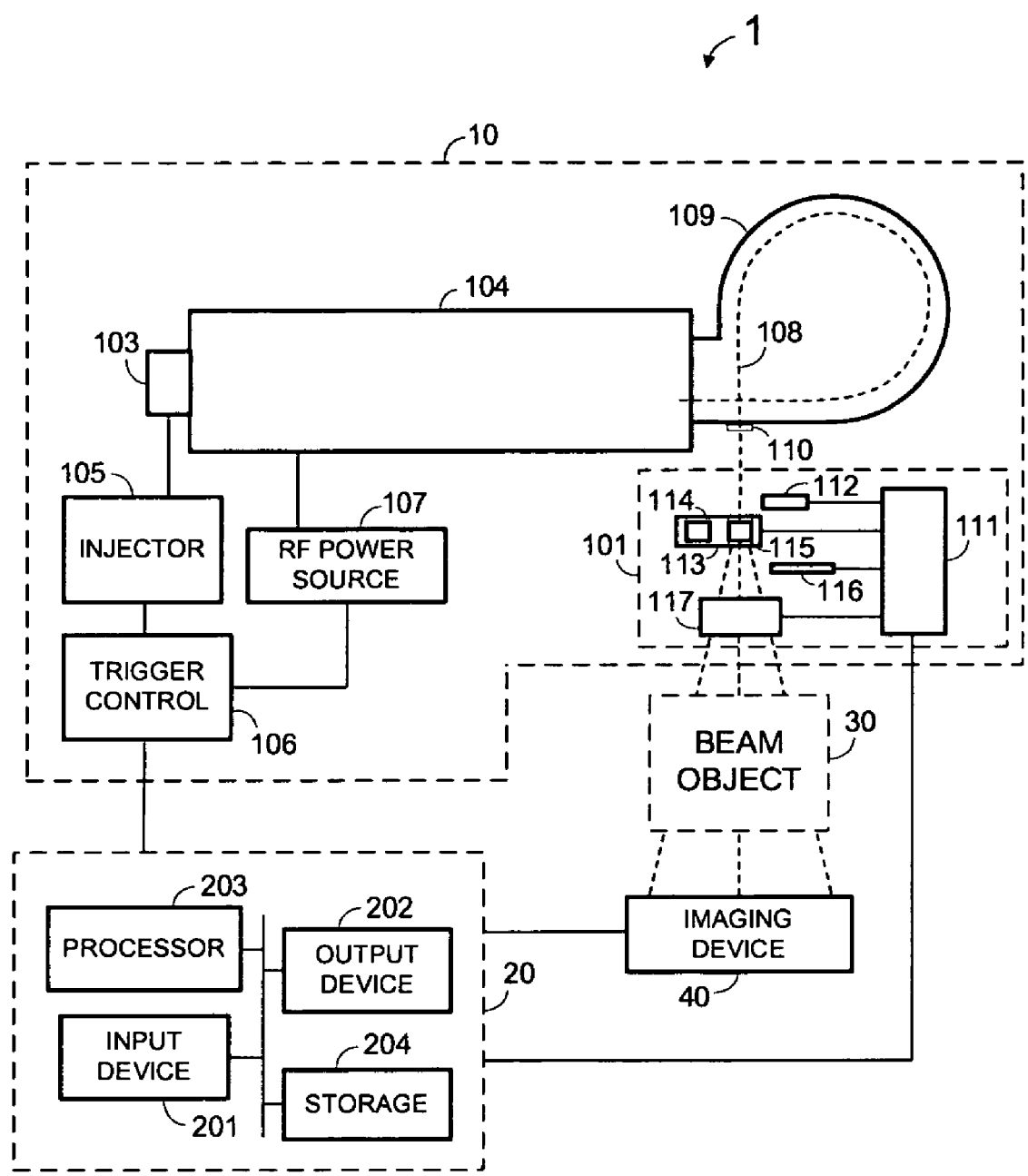
FIG. 7 is a block diagram of a linear accelerator system according to some embodiments.

FIG. 7 is a block diagram of system 1 prior to step 67 according to some embodiments of process steps 60. FIG. 7 is intended to illustrate some of the above-mentioned possible variations of process steps 60. As shown, beam focuser 112 is positioned outside of the path of radiation beam 108. Beam focuser 112 according to the illustrated embodiment comprises a device that increases a focal spot size of beam 108, therefore beam focuser 112 is moved out of the path in order to reduce the focal spot size at step 63.

The FIG. 7 embodiment reflects the completion of steps 64 and 65 as described below. However, step 66 is not performed with respect to the FIG. 7 embodiment because system 1 of FIG. 7 does not include a scatter-reducing filter.

Figure 8:
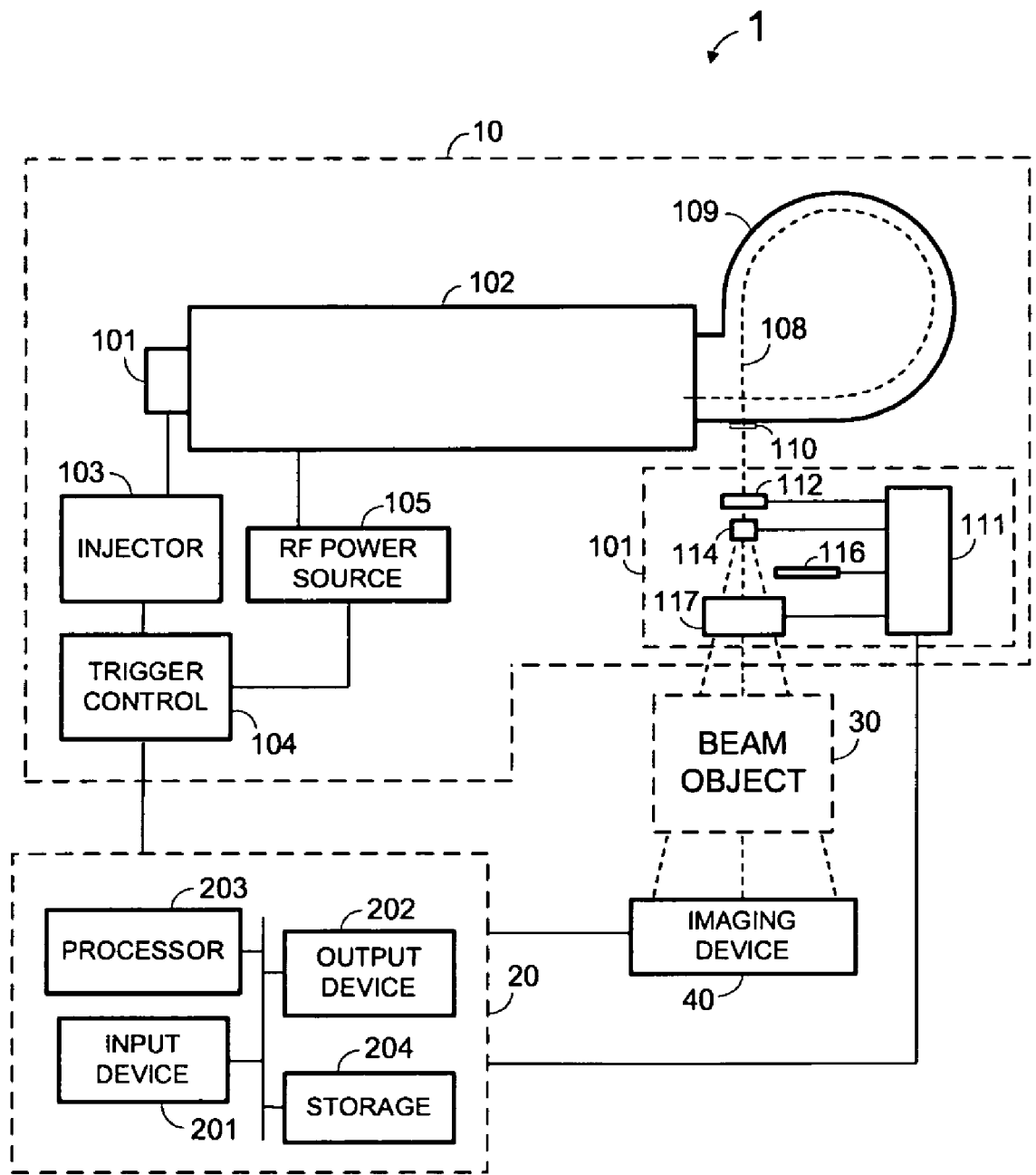
FIG. 8 is block diagram of a linear accelerator system according to some embodiments.

FIG. 8 is a block diagram of system 1 prior to step 67 according to still other embodiments of process steps 60. As shown, beam focuser 112 is positioned in and flattening filter 116 is moved out of the path of radiation beam 108 to operate as described with respect to step 63, step 64, and FIG. 6. The FIG. 8 embodiment includes only a single hi-Z target 114 and therefore does not perform step 65 of process steps 60. Moreover, system 1 of FIG. 8 does not include a scatter-reducing filter, and therefore step 66 is not performed with respect to the FIG. 8 embodiment.

Flow returns to step 61 after step 67. It will now be assumed that an instruction to enter a treatment mode is received at step 61. The instruction may be received in response to operator selection of function keys F1 through F3 during presentation of interface 80 of FIG. 4.

Figure 9:
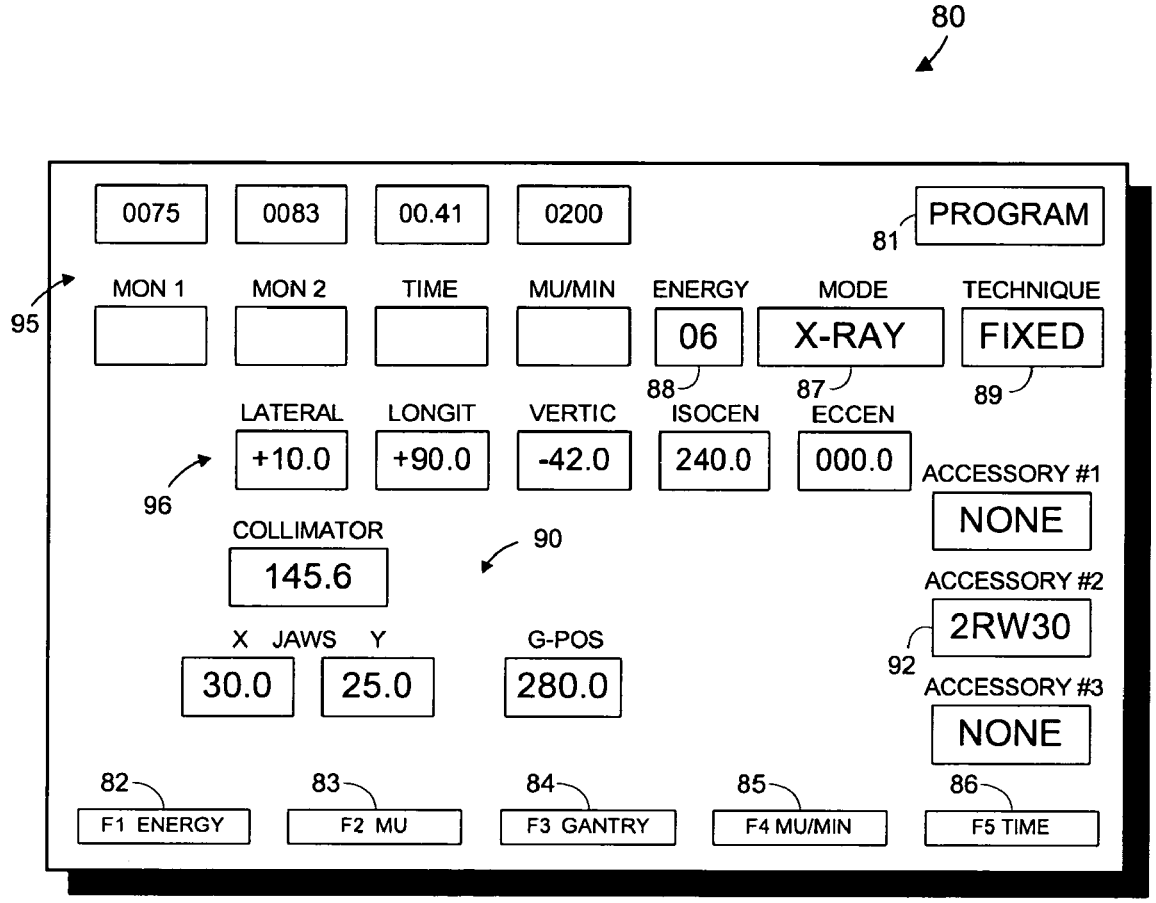
FIG. 9 is an outward view of an interface to receive instructions according to some embodiments.

FIG. 9 illustrates interface 80 after selection of function key F2 (X-FIX-L) according to some embodiments. Function key F2 is associated with low-energy X-ray treatment, therefore fields 87 and 89 are automatically filled to indicate such treatment. The operator may complete field 88 and the top row of fields 95 using sub-interfaces associated with the new labels of fields 82 through 86.

As described above, an operator may place system 1 into a Ready mode by pressing an Accept key of input device 201 after completing all required fields of interface 80 and of any sub-interfaces. Detection of the depressed Accept key may also comprise receiving an instruction to enter a mode at step 61.

Next, at step 62, it is determined that system 1 has been instructed to enter a treatment mode. Accordingly, flow continues to step 68 to increase a focal spot size of a radiation beam. The focal spot size may be increased by deactivating or removing a beam focuser otherwise operable to reduce the focal spot size, or by placing a beam focuser for increasing the focal spot size in the path of the beam. FIG. 2 illustrates the former scenario, with beam focuser 112 being deactivated at step 68.

FIG. 2 also illustrates flattening filter 116 having been moved into the path of beam 108 at step 69, and replacement of target 115 with target 114 at step 70. Some embodiments of process steps 60 further include movement of a scatter-reducing filter out of the path of the radiation beam at step 71. The embodiment of FIG. 2 does not include a scatter-reducing filter.

System 1 executes radiation treatment at step 72. According to some embodiments of step 72, linear accelerator 10 is controlled to emit beam 108 toward treatment head 101 at a specified energy and dose rate suitable for radiation treatment. The specified energy may be substantially identical to the energy used to acquire the image at step 67, and the dose rate may be significantly larger. Beam 108 then impacts target 114 to generate a divergent photon beam having an energy spectrum suitable for treatment. The photon beam passes other elements 117 and beam object 30 to deliver a radiation dose to a target volume of beam object 30. In some embodiments, operator console 20 updates the lower row of fields 95 of interface 80 as shown in FIG. 9 during treatment.

As described with respect to steps 63 through 66, steps 68 through 71 may be performed under the control of control unit 111 in response to signals received from operator console 20. Such control may include transmission of a set of instructions and/or parameters associated with radiation treatment to control unit 111 after step 62. The set may be stored among one or more soft pots of storage 204.

Some embodiments such as that shown in FIG. 2 include performance of only one, two, or three of steps 68 through 71. The steps of 68 through 71 that are performed may occur in any order relative to one another. Two or more of steps 68 through 71 may be performed simultaneously.

According to some embodiments, dosimetric characteristics of beam 108 may be changed in response to an instruction to enter an imaging mode and/or in response to an instruction to enter a treatment mode. For example, in response to an instruction to enter an imaging mode, RF power source 107 and/or bending envelope 109 may be controlled as described in commonly-assigned, co-pending Application Ser. No. (Attorney Docket No. 2005P00148US), entitled Megavoltage Imaging System, such that beam 108 possesses characteristics suitable for imaging.

The several embodiments described herein are solely for the purpose of illustration. Therefore, persons in the art will recognize from this description that other embodiments may be practiced with various modifications and alterations.

What is claimed is:

1. A method comprising:
   receiving a first instruction to enter an imaging mode;
   in response to the first instruction, automatically reducing a focal spot size of a radiation beam, moving a flattening filter out of a path of the radiation beam, moving a first target for photon emission out of the path of the radiation beam and moving a second target for photon emission into the path of the radiation beam, and moving a scatter-reducing filter into the path of the radiation beam;
   receiving a second instruction to enter a first radiation treatment mode; and
   in response to the second instruction, automatically increasing a focal spot size of the radiation beam, moving the flattening filter into the path of the radiation beam, moving the second target out of the path of the radiation beam and moving the first target into the path of the radiation beam, and moving the scatter-reducing filter out of the path of the radiation beam.

2. A method according to claim 1, wherein the second instruction comprises an instruction to enter a photon radiation treatment mode, and further comprising:
   receiving a third instruction to enter an electron radiation treatment mode; and
   in response to the third instruction, automatically moving the first target out of the path of the radiation beam so that neither the first target or the second target is in the path of the radiation beam.

3. A method according to claim 1, wherein reducing the focal spot size of the radiation beam comprises energizing deflector plates disposed adjacent to the path of the radiation beam to focus the radiation beam.

4. A method according to claim 1, wherein an atomic weight of the second target is less than an atomic weight of the first target.

5. A method according to claim 1, wherein, for a given incident electron beam, photons emitted by the second target exhibit a lower average energy than photons emitted by the first target.

6. A method according to claim 1, further comprising:
   presenting an interface to receive the first instruction and the second instruction.

7. A method according to claim 1, further comprising:
   in response to the first instruction, automatically changing dosimetric characteristics of the radiation beam.

8. An apparatus comprising:
   an input device to receive a first instruction to enter an imaging mode, and a second instruction to enter a first radiation treatment mode;
   an accelerator waveguide to emit a radiation beam;
   a first device to reduce a focal spot size of a radiation beam in response to the first instruction, and to increase a focal spot size of the radiation beam in response to the second instruction;
   a second device to move a flattening filter out of a path of the radiation beam in response to the first instruction, and to move the flattening filter into the path of the radiation beam in response to the second instruction;
   a third device to move a first target for photon emission out of the path of the radiation beam and to move a second target for photon emission into the path of the radiation beam in response to the first instruction, and to move the second target out of the path of the radiation beam and to move the first target into the path of the radiation beam in response to the second instruction; and a fourth device to move a scatter-reducing filter into the path of the radiation beam in response to the first instruction, and to move the scatter-reducing filter out of the path of the radiation beam in response to the second instruction.

9. An apparatus according to claim 8, the first device comprising:
   deflector plates disposed adjacent to the path of the radiation beam.

10. An apparatus according to claim 8, wherein an atomic weight of the second target is less than an atomic weight of the first target.

11. An apparatus according to claim 8, wherein, for a given incident electron beam, photons emitted by the second target exhibit a lower average energy than photons emitted by the first target.

12. An apparatus according to claim 8, further comprising:
   a fifth device to change dosimetric characteristics of the radiation beam in response to the first instruction.

13. A medium storing program code, the program code comprising:
   code to receive a first instruction to enter an imaging mode;
   code to, in response to the first instruction, automatically reduce a focal spot size of a radiation beam, move a flattening filter out of a path of the radiation beam, move a first target for photon emission out of the path of the radiation beam and move a second target for photon emission into the path of the radiation beam, and move a scatter-reducing filter into the path of the radiation beam;
   code to receive a second instruction to enter a first radiation treatment mode; and
   code to, in response to the second instruction, automatically perform at least one of: increase a focal spot size of the radiation beam, move the flattening filter into the path of the radiation beam, move the second target out of the path of the radiation beam and move the first target into the path of the radiation beam, and move the scatter-reducing filter out of the path of the radiation beam.

14. A medium according to claim 13. wherein the second instruction comprises an instruction to enter a photon radiation treatment mode, and the program code further comprising:
   code to receive a third instruction to enter an electron radiation treatment mode; and
   code to, in response to the third instruction, automatically move the first target out of the path of the radiation beam so that neither the first target or the second target is in the path of the radiation beam.

15. A medium according to claim 13, wherein the code to reduce the focal spot size of the radiation beam comprises code to energize deflector plates disposed adjacent to the path of the radiation beam to focus the radiation beam.

16. A medium according to claim 13, wherein an atomic weight of the second target is less than an atomic weight of the first target.

17. A medium according to claim 13, wherein, for a given incident electron beam, photons emitted by the second target exhibit a lower average energy than photons emitted by the first target.

18. A medium according to claim 13, the program code further comprising:
   code to present an interface to receive the first instruction and the second instruction.

19. A medium according to claim 13, the program code further comprising:
   code to, in response to the first instruction, automatically change dosimetric characteristics of the radiation beam.

\* \* \* \* \*